(12) United States Patent
Takamatsu et al.

(10) Patent No.: US 8,748,654 B2
(45) Date of Patent: Jun. 10, 2014

(54) METHOD FOR PRODUCING TOLYLENE DIISOCYANATE

(75) Inventors: Koji Takamatsu, Ichihara (JP); Kazuhiro Kosumi, Omuta (JP); Takeshi Fukuda, Kurume (JP); Masaaki Sasaki, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 14/115,852

(22) PCT Filed: Apr. 6, 2012

(86) PCT No.: PCT/JP2012/059491
§ 371 (c)(1),
(2), (4) Date: Nov. 5, 2013

(87) PCT Pub. No.: WO2012/157366
PCT Pub. Date: Nov. 22, 2012

(65) Prior Publication Data
US 2014/0073811 A1    Mar. 13, 2014

(30) Foreign Application Priority Data
May 18, 2011  (JP) ................................. 2011-111786

(51) Int. Cl.
*C07C 263/00* (2006.01)
*C07C 263/04* (2006.01)
*C07C 263/06* (2006.01)
*C07C 263/20* (2006.01)

(52) U.S. Cl.
CPC ............. *C07C 263/00* (2013.01); *C07C 263/04* (2013.01); *C07C 263/06* (2013.01); *C07C 263/20* (2013.01)
USPC ......................................... 560/345; 560/344

(58) Field of Classification Search
CPC .. C07C 263/00; C07C 263/04; C07C 263/06; C07C 263/20
USPC .................................................. 560/344, 345
See application file for complete search history.

(56) References Cited

U.S. PATENT DOCUMENTS

| | | | |
|---|---|---|---|
| 4,290,970 | A | 9/1981 | Merger et al. |
| 5,087,739 | A | 2/1992 | Bohmholdt et al. |
| 5,783,727 | A | 7/1998 | Parron et al. |
| 6,255,529 | B1 | 7/2001 | Nagase et al. |
| 2003/0012710 | A1 | 1/2003 | Nishida et al. |
| 2012/0271067 | A1 | 10/2012 | Shimokawatoko et al. |

FOREIGN PATENT DOCUMENTS

| | | |
|---|---|---|
| JP | 56-65858 A | 6/1981 |
| JP | 2-101057 A | 4/1990 |
| JP | 09-151270 | 6/1997 |
| JP | 10-507738 A | 7/1998 |
| JP | 10-279539 A | 10/1998 |
| WO | WO-2011/078000 A1 | 6/2011 |

OTHER PUBLICATIONS

PCT International Preliminary Report on Patentability, with PCT Notification of Transmittal of Translation of the International Preliminary Report on Patentability, issued in application No. PCT/JP/2012/059491, dated Nov. 28, 2013.
PCT International Preliminary Report on Patentability, with PCT Notification Concerning Transmittal of International Preliminary Report on Patentability, issued in application No. PCT/JP/2012/059491 on Nov. 28, 2013.
International Search Report received in PCT/JP2012/059491 dated Jul. 3, 2012.

*Primary Examiner* — Jafar Parsa
(74) *Attorney, Agent, or Firm* — Foley & Lardner LLP

(57) ABSTRACT

A method for producing tolylene diisocyanate includes: mixing a first diaminotoluene containing 2,4-diaminotoluene and 2,6-diaminotoluene at a first isomer ratio and a second diaminotoluene containing 2,4-diaminotoluene and/or 2,6-diaminotoluene at a second isomer ratio that is different from the first isomer ratio so as to prepare mixed diaminotoluene; producing tolylene dicarbamate by reaction of the mixed diaminotoluene, urea and/or N-unsubstituted carbamic acid ester and alcohol; and thermally decomposing the tolylene dicarbamate.

3 Claims, 1 Drawing Sheet

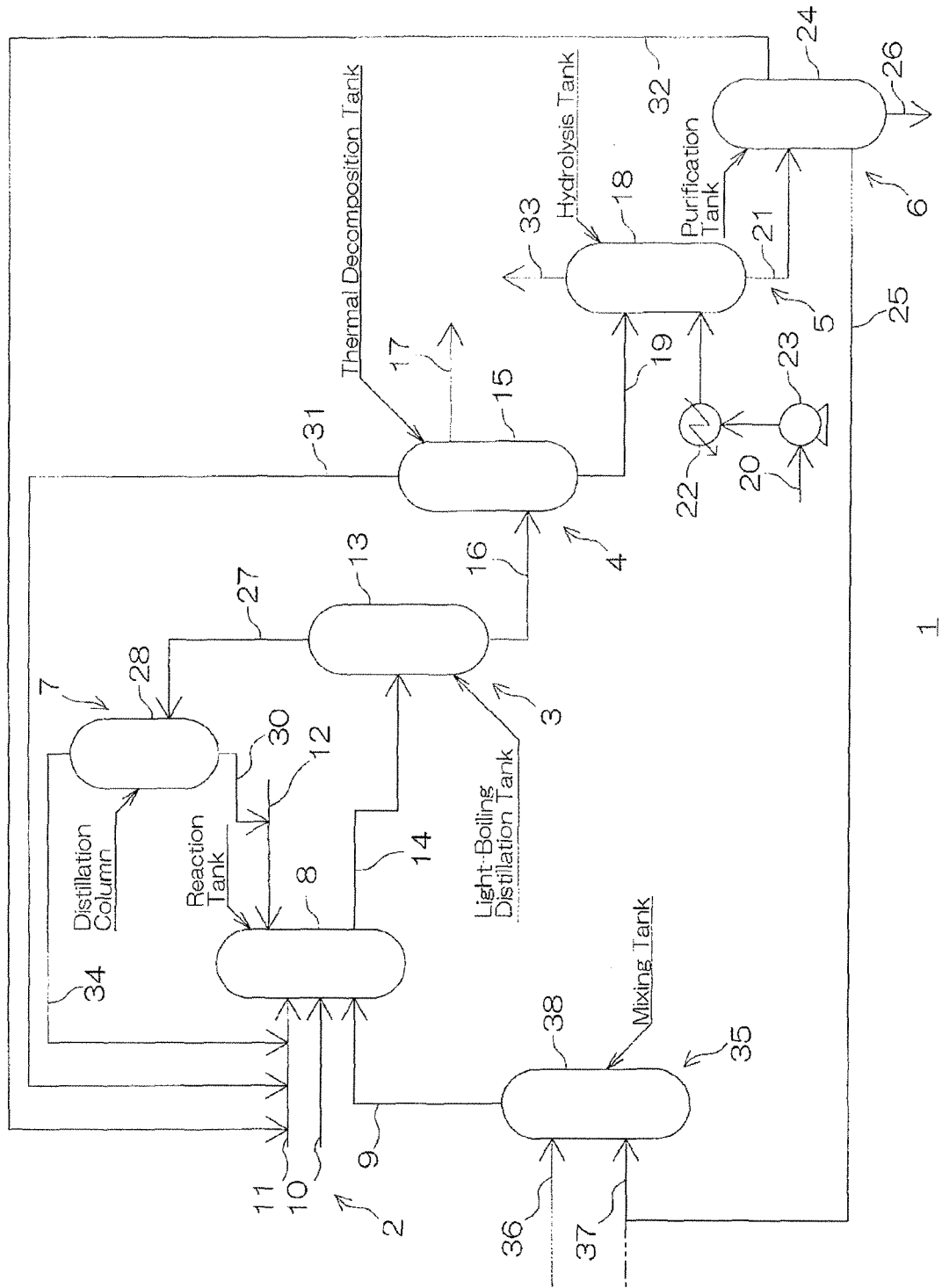

METHOD FOR PRODUCING TOLYLENE DIISOCYANATE

This application is the National Phase of PCT/JP2012/059491, filed Apr. 6, 2012, which claims priority to Japanese Application No. 2011-111786, filed May 18, 2011, the disclosures of which are hereby incorporated by reference in their entirety.

TECHNICAL FIELD

The present invention relates to a method for producing tolylene diisocyanate, and more particularly to a method for producing tolylene diisocyanate containing 2,4-tolylene diisocyanate and 2,6-tolylene diisocyanate at a desired isomer ratio.

BACKGROUND ART

Tolylene diisocyanate is widely known as versatile isocyanate for use as a raw material for polyurethane, polyurea and the like.

Conventionally, tolylene diisocyanate has been industrially produced by reaction (phosgene method) between diaminotoluene and phosgene. However, phosgene has various problems such as being highly toxic and troublesome in handling, and requiring careful attention to corrosion of the equipment because it by-produces a large amount of hydrochloric acid. Accordingly, there is a need to develop industrial production methods for tolylene diisocyanate that can replace the phosgene method.

Generally known tolylene diisocyanate production methods that do not use phosgene include a method (carbonate method) in which amine is carbamated with dialkyl carbonate and thereafter the obtained carbamate is thermally decomposed, and a method (urea method) in which amine is carbamated with urea, N-unsubstituted carbamic acid ester and the like and thereafter the obtained carbamate is thermally decomposed.

For production of aromatic di- and/or polyisocyanate, for example, a method has been proposed in which primary aromatic di- and/or polyamine and O-alkylcarbamide acid ester are reacted in the presence of urea and alcohol to give aryl-di- and/or polyurethane, and the obtained polyurethane is thermally decomposed.

In particular, for production of tolylene diisocyanate, specifically a method has been proposed in which toluoylene diisocyanate is produced by causing 2,4-diaminotoluol, carbamide acid ethyl ester and ethanol to be reacted to give 2,4-di-(ethoxycarbonylamino)-toluol, and thermally decomposing the obtained 2,4-di-(ethoxycarbonylamino)-toluol (see, for example, Patent Document 1 below).

According to such methods, tolylene diisocyanate can be produced without using phosgene.

CITATION LIST

Patent Document

Patent Document 1: Japanese Unexamined Patent Publication No. S56-65858

DISCLOSURE OF THE INVENTION

Problems to be Solved

On the other hand, tolylene diisocyanate for industrial use is required to contain isomers such as 2,4-tolylene diisocyanate and 2,6-tolylene diisocyanate at a desired isomer ratio.

However, when, in the carbonate method and the urea method, diaminotoluenes having the same isomer ratio (e.g., 2,4-diaminotoluene/2,6-diaminotoluene=80/20 (molar ratio)) as the desired isomer ratio of tolylene diisocyanate (e.g., 2,4-tolylene diisocyanate/2,6-tolylene diisocyanate=80/20 (molar ratio)) are used as raw materials, a problem arises in that the isomer ratio of the obtained tolylene diisocyanate is different from the desired isomer ratio.

It is an object of the present invention to provide a tolylene diisocyanate production method for producing tolylene diisocyanate containing 2,4-tolylene diisocyanate and 2,6-tolylene diisocyanate at a desired isomer ratio.

Means for Solving the Problem

A method for producing tolylene diisocyanate of the present invention is a method for producing tolylene diisocyanate containing 2,4-tolylene diisocyanate and 2,6-tolylene diisocyanate at a target isomer ratio, the method including: mixing a first diaminotoluene containing 2,4-diaminotoluene and 2,6-diaminotoluene at a first isomer ratio and a second diaminotoluene containing 2,4-diaminotoluene and/or 2,6-diaminotoluene at a second isomer ratio that is different from the first isomer ratio so as to prepare mixed diaminotoluene; producing tolylene dicarbamate by reaction of the mixed diaminotoluene, urea and/or N-unsubstituted carbamic acid ester and alcohol; and thermally decomposing the tolylene dicarbamnate.

In the method for producing tolylene diisocyanate of the present invention, it is preferable that the first isomer ratio is 2,4-diaminotoluene/2,6-diaminotoluene (molar ratio)=79 to 81/21 to 19, the second isomer ratio is set such that a proportion of 2,4-diaminotoluene is higher than a proportion of 2,4-diaminotoluene in the first isomer ratio, and in the mixing step, the second diaminotoluene is mixed in an amount of 1 to 30 parts by mass per 100 parts by mass of the first diaminotoluene.

Also, in the method for producing tolylene diisocyanate of the present invention, it is preferable that the second diaminotoluene is produced by decomposing isocyanate residues, which are obtained by separating tolylene diisocyanate and alcohol from a decomposition solution resulting from the thermal decomposition reaction of the tolylene dicarbamate in the thermal decomposition step, by contact with high pressure and high temperature water.

Effect of the Invention

According to the method for producing tolylene diisocyanate of the present invention, a first diaminotoluene and a second diaminotoluene having different 2,4-diaminotoluene/2,6-diaminotoluene isomer ratios are mixed to prepare mixed diaminotoluene, and the mixed diaminotoluene is carbamated and thermally decomposed, whereby tolylene diisocyanate containing 2,4-tolylene diisocyanate and 2,6-tolylene diisocyanate at a target isomer ratio can be obtained.

BRIEF DESCRIPTION OF THE DRAWINGS

FIG. 1 is a schematic configuration diagram showing one embodiment of a plant in which a method for producing tolylene diisocyanate of the present invention is used.

EMBODIMENT OF THE INVENTION

According to the method for producing tolylene diisocyanate of the present invention, tolylene dicarbamate, obtained by reaction of mixed diaminotoluene prepared by mixing a first diaminotoluene and a second diaminotoluene having different 2,4-diaminotoluene/2,6-diaminotoluene isomer ratios, urea and/or N-unsubstituted carbamic acid ester and alcohol, is thermally decomposed, whereby tolylene diisocyanate containing 2,4-tolylene diisocyanate and 2,6-tolylene diisocyanate at a target isomer ratio is produced.

Specifically, in this method, first, the first diaminotoluene and the second diaminotoluene are mixed to prepare mixed diaminotoluene such that the resulting tolylene diisocyanate contains 2,4-tolylene diisocyanate and 2,6-tolylene diisocyanate at a target isomer ratio (mixing step).

The first diaminotoluene contains 2,4-diaminotoluene and 2,6-diaminotoluene at a first isomer ratio.

The first isomer ratio can be, for example, 2,4-diaminotoluene/2,6-diaminotoluene (molar ratio)=75 to 85/25 to 15, preferably 77 to 83/23 to 17, or more preferably 79 to 81/21 to 19.

There is no particular limitation on the first diaminotoluene, and for example, those available as industrial raw materials can be used.

The second diaminotoluene contains 2,4-diaminotoluene and/or 2,6-diaminotoluene at a second isomer ratio that is different from the first isomer ratio.

The second isomer ratio is preferably such that the proportion (molar ratio) of 2,4-diaminotoluene is higher than the proportion (molar ratio) of 2,4-diaminotoluene in the first isomer ratio, or more preferably the proportion (molar ratio) of 2,4-diaminotoluene is higher than the proportion (molar ratio) of 2,4-diaminotoluene in the first isomer ratio by 5 to 25. Specifically, the proportion (molar ratio) of 2,4-diaminotoluene is, for example, 80 or greater, preferably 85 or greater, or more preferably 90 or greater. The proportion (molar ratio) of 2,6-diaminotoluene is, for example, 20 or less, preferably 15 or less, or more preferably 10 or less.

There is no particular limitation on the second diaminotoluene. As will be described in detail later; diaminotoluene (decomposed diaminotoluene) obtained as a result of decomposition of isocyanate residues, which will be described later, or those available as industrial raw materials can be used.

The mixing proportions of the first diaminotoluene and the second diaminotoluene are adjusted such that the resulting tolylene diisocyanate contains 2,4-tolylene diisocyanate and 2,6-tolylene diisocyanate at a target isomer ratio.

The target isomer ratio in the tolylene diisocyanate is, for example, 2,4-tolylene diisocyanate/2,6-tolylene diisocyanate (molar ratio)=75 to 85/25 to 15, preferably 77 to 83/23 to 17, or more preferably 79 to 81/21 to 19.

In this case, the mixing proportions of the first diaminotoluene and the second diaminotoluene are set such that the proportion of the second diaminotoluene is, for example, 1 to 50 parts by mass, preferably 1 to 30 parts by mass, more preferably 1 to 20 parts by mass, or even more preferably 1 to 10 parts by mass per 100 parts by mass of the first diaminotoluene.

As long as the mixing proportions of the first diaminotoluene and the second diaminotoluene fall within the above ranges, decomposed diaminotoluene, which will be described later, can be efficiently used, and tolylene diisocyanate can be efficiently produced.

The thus-obtained mixed diaminotoluene contains 2,4-diaminotoluene and 2,6-diaminotoluene.

The 2,4-diaminotoluene/2,6-diaminotoluene isomer ratio in the mixed diaminotoluene is set such that the proportion (molar ratio) of 2,4-diaminotoluene is higher than the proportion (molar ratio) of 2,4-tolylene diisocyanate in the target isomer ratio of the tolylene diisocyanate. Specifically, 2,4-tolylene diisocyanate/2,6-tolylene diisocyanate (molar ratio)=75 to 88/25 to 12, preferably 77 to 85/23 to 15, or more preferably 79 to 82/21 to 18.

Next, in this method, the mixed diaminotoluene, urea and/or N-unsubstituted carbamic acid ester and alcohol are reacted to produce tolylene dicarbamate (carbamate producing step).

The N-unsubstituted carbamic acid ester is a carbamic acid ester in which a nitrogen atom of a carbamoyl group is not substituted with a functional group (i.e., the nitrogen atom is bonded to two hydrogen atoms and one carbon atom), and is represented, for example, by the following general formula (1):

$$R^1O—CO—NH_2 \quad (1),$$

where $R^1$ represents an alkyl group, or an aryl group which may have a substituent.

Examples of the alkyl group represented by $R^1$ in the above formula (1) include: a linear or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms such as cyclohexyl and cyclododecyl.

As the alkyl group represented by $R^1$, it is preferable to use a linear or branched saturated hydrocarbon group having 1 to 8 carbon atoms, more preferably a linear or branched saturated hydrocarbon group having 2 to 6 carbon atoms, or even more preferably a linear saturated hydrocarbon group having 2 to 6 carbon atoms.

Examples of the N-unsubstituted carbamic acid ester in which $R^1$ represents an alkyl group in the above formula (1) include: N-unsubstituted carbamic acid esters containing a saturated hydrocarbon such as methyl carbamate, ethyl carbamate, n-propyl carbamate, iso-propyl carbamate, n-butyl carbamate, iso-butyl carbamate, sec-butyl carbamate, tert-butyl carbamate, pentyl carbamate, hexyl carbamate, heptyl carbamnate, octyl carbamate, iso-octyl carbamnate, and 2-ethylhexyl carbamate; and N-unsubstituted carbamic acid esters containing an alicyclic saturated hydrocarbon such as cyclohexyl carbamate and cyclododecyl carbamate.

Examples of the aryl group which may have a substituent, represented by $R^1$ in the above formula (1), include aryl groups having 6 to 18 carbon atoms such as phenyl, tolyl, xylyl, biphenyl, naphthyl, anthryl, and phenanthryl. Examples of the substituent include a hydroxyl group, a halogen atom (e.g., chlorine, fluorine, bromine, and iodine), a cyano group, an amino group, a carboxyl group, an alkoxy group (e.g., an alkoxy group having 1 to 4 carbon atoms such as a methoxy, an ethoxy, a propoxy, or a butoxy group), an aryloxy group (e.g., a phenoxy group etc.), an alkylthio group (e.g., an alkylthio group having 1 to 4 carbon atoms such as a methylthio, an ethylthio, a propylthio, or a butylthio group), and an arylthio group (e.g., a phenylthio group). When the substituents are multiply substituted at the aryl group, the substituents may be the same or different from each other.

Examples of the N-unsubstituted carbamic acid ester whose $R^1$ represents an aryl group which may have a substituent in the above formula (1) include N-unsubstituted carbamic acid esters containing an aromatic hydrocarbon such as phenyl carbamate, tolyl carbamate, xylyl carbamate, biphenyl carbamate, naphthyl carbamate, anthryl carbamate, and phenanthryl carbamate.

These N-unsubstituted carbamic acid esters can be used singly or in a combination of two or more.

As the N-unsubstituted carbamic acid ester, it is preferable to use N-unsubstituted carbamic acid ester in which $R^1$ represents an alkyl group in the above formula (1).

Furthermore, as the N-unsubstituted carbamic acid ester used as a raw material component for the carbamate-forming reaction, it is preferable to include N-unsubstituted carbamic acid ester obtained by further separating from low boiling components (described later) which have been separated after the carbamate-forming reaction, the detail of which will be described later.

The alcohol is, for example, a primary to tertiary monohydric alcohol and is, for example, represented by the following general formula (2):

$$R^1\text{—OH} \quad (2),$$

where $R^1$ is as defined for $R^1$ in the above formula (1).

In the above formula (2), $R^1$ is as defined for $R^1$ in the above formula (1), or in other words, represents an alkyl group, or an aryl group which may have a substituent.

Examples of the alcohol in which $R^1$ represents the alkyl group in the above formula (2) include: alcohols containing a linear or branched saturated hydrocarbon, such as methanol, ethanol, n-propanol, iso-propanol, n-butanol (1-butanol), iso-butanol, sec-butanol, tert-butanol, pentanol, hexanol, heptanol, octanol, iso-octanol, and 2-ethylhexanol; and alcohols containing an alicyclic saturated hydrocarbon, such as cyclohexanol and cyclododecanol.

Furthermore, examples of the alcohol whose $R^1$ represents the above-described aryl group which may have a substituent in the above formula (2) include phenol, hydroxytoluene, hydroxyxylene, biphenyl alcohol, naphthalenol, anthracenol, and phenanthrenol.

These alcohols can be used singly or in a combination of two or more.

As the alcohol, in the above formula (2), it is preferable to use an alcohol in which $R^1$ represents an alkyl group, more preferably an alcohol in which $R^1$ represents an alkyl group having 1 to 8 carbon atoms, or even more preferably an alcohol in which $R^1$ represents an alkyl group having 2 to 6 carbon atoms.

As the alcohol used as a raw material component for the carbamate-forming reaction, it is preferable to include an alcohol (described later) obtained by hydrolyzing the isocyanate residues.

Furthermore, other preferred examples of the alcohol used as a raw material component for the carbamate-forming reaction include an alcohol (described later) by-produced when N-unsubstituted carbamic acid ester is used as a raw material component in the carbamate-forming reaction, and an alcohol (described later) separated from the decomposition solution resulting from the thermal decomposition reaction of the tolylene dicarbamate.

In this method, the mixed diaminotoluene, urea and/or N-unsubstituted carbamic acid ester, and alcohol described above are blended and the blended mixture is allowed to react preferably in a liquid phase.

The amounts of the mixed diaminotoluene, urea and/or N-unsubstituted carbamic acid ester, and alcohol are not particularly limited and can be appropriately selected over a relatively wide range.

Usually, the amounts of the urea and the N-unsubstituted carbamic acid ester, and the amount of the alcohol may be equimolar or more to the amount of the amino group in the mixed diaminotoluene, so that the urea and/or the N-unsubstituted carbamic acid ester, and the alcohol themselves can also be used as reaction solvents in this reaction.

When the urea and/or the N-unsubstituted carbamic acid ester and the alcohol also serve as the reaction solvents, excess amounts of the urea and/or the N-unsubstituted carbamic acid ester and the alcohol are used as required. Large excess amounts thereof, however, increase consumption energy in the separation step after the reaction, which may be unsuitable for industrial production.

Therefore, from the viewpoint of improving the yield of the tolylene dicarbamate, the amount(s) of the urea and/or the N-unsubstituted carbamic acid ester is/are of the order of 0.5 to 20 times moles, preferably 1 to 10 times moles, or more preferably 1 to 5 times moles with respect to one amino group of the mixed diaminotoluene, and the amount of the alcohol is of the order of 0.5 to 100 times moles, preferably 1 to 20 times moles, or more preferably 1 to 10 times moles, with respect to one amino group of the mixed diaminotoluene.

In this reaction, although a reaction solvent is not necessarily required, for example, when reaction raw materials are solid or when a reaction product is deposited, blending of a reaction solvent such as aliphatic hydrocarbons, aromatic hydrocarbons, ethers, nitriles, aliphatic halogenated hydrocarbons, amides, nitro compounds, N-methylpyrrolidinone, N,N-dimethylimidazolidinone, dimethyl sulfoxide can improve operability.

The amount of the reaction solvent is not particularly limited as long as it is sufficient for the tolylene dicarbamate as a desired product to be dissolved. Industrially, the amount of the reaction solvent is preferably reduced as much as possible because it is necessary to recover the reaction solvent from the reaction solution and reduce the energy consumed for the recovery as much as possible, and also because a large amount of the reaction solvent can decrease substrate concentration on the reaction and slow the reaction rate. More specifically, the amount of the reaction solvent is usually in the range of 0 to 500 parts by mass, or preferably 0 to 100 parts by mass, per 1 part by mass of the mixed diaminotoluene.

In this reaction, the reaction temperature is appropriately selected from the range of 100 to 350° C., or preferably 150 to 300° C. When the reaction temperature is lower than this range, the reaction rate may decrease. On the other hand, when it is higher than this range, a side reaction increases, so that the yield of the tolylene dicarbamate may be reduced.

The reaction is usually carried out under atmospheric pressure. However, when the boiling point of the component in the reaction solution is lower than the reaction temperature, the reaction may be carried out under an increased pressure or, if necessary, under a reduced pressure.

The reaction time is in the range of, for example, 0.1 to 20 hours, or preferably 0.5 to 10 hours. When the reaction time is shorter than this range, the yield of the tolylene dicarbamate may be reduced. On the other hand, when it is longer than this range, the reaction is unsuitable for industrial production.

In this method, a catalyst can also be used.

There is no particular limitation on the catalyst, and examples thereof include lithium methanolate, lithium ethanolate, lithium propanolate, lithium butanolate, sodium methanolate, potassium-tert-butanolate, magnesium methanolate, calcium methanolate, tin(I) chloride, tin(IV) chloride, lead acetate, lead phosphate, antimony(III) chloride, antimony(V) chloride, aluminum acetylacetonate, aluminum-isobutylate, aluminum trichloride, bismuth(III) chloride, copper(II) acetate, copper(II) sulfate, copper(II) nitrate, bis (triphenyl-phosphinoxide)-copper(II) chloride, copper molybdate, silver acetate, gold acetate, zinc oxide, zinc chloride, zinc acetate, zinc acetonylacetate, zinc octanoate, zinc oxalate, zinc hexylate, zinc benzoate, zinc undecylenate, cerium(IV) oxide, uranyl acetate, titanium tetraisopropanolate, titanium tetrabutanolate, titanium tetrachloride, titanium tetraphenolate, titanium naphthenate, vanadium(II) chloride, vanadium acetylacetonate, chromium(III) chloride, molybdenum(VI) oxide, molybdenum acetylacetonate, tungsten (VI) oxide, manganese(II) chloride, manganese(II) acetate, manganese(III) acetate, iron(II) acetate, iron(II) acetate, iron phosphate, iron oxalate, iron(II) chloride, iron(II) bromide, cobalt acetate, cobalt chloride, cobalt sulfate, cobalt naphthenate, nickel chloride, nickel acetate, and nickel naphthenate.

Furthermore, examples of the catalyst include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts can be used singly or in a combination of two or more.

The amount of the catalyst is in the range of, for example, 0.000001 to 0.1 mol, or preferably 0.00005 to 0.05 mol, per 1 mol of the mixed diaminotoluene. Even if the amount of the catalyst is more than the above range, no further remarkable reaction enhancing effect is observed, and at the same time, cost may increase due to an increase in the amount. On the other hand, when the amount is less than the above range, the reaction enhancing effect may not be obtained.

The method for adding the catalyst is not particularly limited, and any of package addition, continuous addition, and intermittent addition in portions can be used as long as it does not affect the reaction activity.

Then, this reaction may be carried out, for example, by charging the mixed diaminotoluene, urea and/or N-unsubstituted carbamic acid ester, alcohol, if necessary, a catalyst and a reaction solvent, in a reaction vessel under the above-described conditions, and stirring or mixing the charged mixture. Tolylene dicarbamate containing 2,4-tolylene dicarbamate and 2,6-tolylene dicarbamate is produced as a main product.

Also, in this reaction, ammonia is by-produced.

Also, when N-unsubstituted carbamic acid ester is blended in this reaction, for example, an alcohol represented by the following general formula (3) is by-produced.

$$R^1\text{—OH} \tag{3}$$

where $R^1$ is as defined for $R^1$ in the above formula (1).

Also, in this reaction, for example, an N-unsubstituted carbamic acid ester represented by the following general formula (4) is by-produced.

$$R^1O\text{—CO—NH}_2 \tag{4}$$

where $R^1$ is as defined for $R^1$ in the above formula (1).

In this reaction, either of a batch reaction process or a continuous reaction process can be adopted.

Next, in this method, tolylene dicarbamate is separated from the obtained reaction solution by a known method, and at the same time, for example, excess (unreacted) urea and/or N-unsubstituted carbamic acid ester and excess (unreacted) alcohol; and the by-produced alcohol (the above formula (3)) and N-unsubstituted carbamic acid ester (the above formula (4)) are separated as low boiling components (light-boiling fractions).

Preferably, the alcohol (excess (unreacted) alcohol and by-produced alcohol) roughly separated from the low boiling components (light-boiling fractions) is used as a raw material component for the carbamate-forming reaction.

Therefore, the alcohol roughly separated from the low boiling components (light-boiling fractions) can be industrially effectively used.

Also, preferably, N-unsubstituted carbamic acid ester roughly separated from the low boiling components (light-boiling fractions) is used as a raw material component for the carbamate-forming reaction.

Therefore, the N-unsubstituted carbamic acid ester roughly separated from the low boiling components (light-boiling fractions) can be industrially effectively used.

Then, in this method, the obtained tolylene dicarbamate is thermally decomposed to produce tolylene diisocyanate and alcohol (thermal decomposition step).

Specifically, in this method, for example, the tolylene dicarbamate obtained by the above-described method is thermally decomposed, and tolylene diisocyanate containing 2,4-tolylene diisocyanate and 2,6-tolylene diisocyanate at the above-described target isomer ratio and an alcohol represented by the following general formula (5) which is a by-product are produced.

$$R^1\text{—OH} \tag{5}$$

where $R^1$ is as defined for $R^1$ in the above formula (1).

There is no particular limitation on the thermal decomposition. Any known decomposition method such as a liquid phase method or a vapor phase method can be used.

In the vapor phase method, the tolylene diisocyanate and alcohol produced by the thermal decomposition can be separated from a gaseous product mixture by fractional condensation. In the liquid phase method, the tolylene diisocyanate and alcohol produced by the thermal decomposition can be separated, for example, by distillation or using a solvent and/or inert gas as a support substance.

As the thermal decomposition, a liquid phase method is preferable from the viewpoint of workability.

In such method, the tolylene dicarbamate is thermally decomposed preferably in the presence of an inert solvent.

The inert solvent is not particularly limited as long as it dissolves at least the tolylene dicarbamate, is inert to the tolylene dicarbamate and the tolylene diisocyanate, and remains unreacted (i.e., stable) during the thermal decomposition. For efficient thermal decomposition reaction, the inert solvent preferably has a higher boiling point than the tolylene diisocyanate to be produced.

As such inert solvent, aromatic hydrocarbons may be used. Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264-266° C.), triphenylmethane (boiling point: 358 to 359° C. (754 mmHg)), 1-phenylnaphthalene (boiling point: 324-325° C.), 2-phenylnaphthalene (boiling point: 357-358° C.), and biphenyl (boiling point: 255° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

Furthermore, examples of the inert solvent include esters (e.g., dioctyl phthalate, didecyl phthalate, and didodecyl phthalate) and aliphatic hydrocarbons which are commonly used as a heat transfer medium.

These inert solvents can be used singly or in a combination of two or more.

The amount of the inert solvent is in the range of 0.001 to 100 parts by mass, preferably 0.01 to 80 parts by mass, or more preferably 0.1 to 50 parts by mass, per 1 part by mass of the tolylene dicarbamate.

In the thermal decomposition, for example, the inert solvent is blended with the tolylene dicarbamate, and the blended tolylene dicarbamate is thermally decomposed. Thereafter, the inert solvent is separated and recovered, and then again can be blended with the tolylene dicarbamate in the thermal decomposition.

Since the thermal decomposition reaction of the tolylene dicarbamate in the liquid phase method is a reversible reaction, preferably the tolylene dicarbamate is thermally decomposed and, to suppress a reverse reaction (i.e., the urethane-forming reaction between the tolylene diisocyanate and the alcohol represented by the above formula (5)) to the thermal decomposition reaction, at the same time, the tolylene diisocyanate and/or the alcohol represented by the above formula (5) are drawn out of the reaction mixture (decomposition solution) to be separated.

Preferable reaction conditions for the thermal decomposition reaction include reaction conditions in which the tolylene dicarbamate can be thermally decomposed in an excellent manner, and at the same time, the tolylene diisocyanate and alcohol (the above formula (5)) produced by the thermal decomposition evaporate, whereby the tolylene dicarbamate and the tolylene diisocyanate fail to reach equilibrium, and further, a side reaction such as polymerization of tolylene diisocyanates is suppressed.

As the reaction conditions, more specifically, the thermal decomposition temperature is usually 350° C. or lower, preferably from 80 to 350° C., or more preferably from 100 to 300° C. At a thermal decomposition temperature lower than 80° C., a practical reaction rate may not be obtained. On the other hand, at a thermal decomposition temperature higher than 350° C., an undesired side reaction such as polymerization of tolylene diisocyanates may occur. The pressure during the thermal decomposition reaction is preferably a pressure for allowing the alcohol produced to be vaporized at the thermal decomposition reaction temperature specified above. For practical use, the pressure is preferably in the range of 0.133 to 90 kPa in terms of equipment and utilities.

In this method, a catalyst may be added if necessary.

Although it depends on the kind of catalyst, the catalyst may be added at any time such as during the above-described reaction, before or after distillation and separation after the reaction, and before or after separation of the tolylene dicarbamate.

As the catalyst used for the thermal decomposition, at least one metal selected from the group consisting of Sn, Sb, Fe, Co, Ni, Cu, Cr, Ti, Pb, Mo, and Mn, or a metallic compound thereof such as oxide, halide, carboxylate, phosphate, and organometallic compound, used for the urethane-forming reaction of a tolylene diisocyanate and a hydroxyl group is used. Among them, Fe, Sn, Co, Sb, and Mn are preferably used in the thermal decomposition because they exhibit the effect of suppressing the production of by-product.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetylacetonate thereof.

The amount of the catalyst is in the range of 0.0001 to 5% by mass, or preferably 0.001 to 1% by mass, per the reaction solution, as a metal or a compound thereof.

The thermal decomposition reaction can be carried out by a batch reaction process in which the tolylene dicarbamate, the catalyst, and the inert solvent are charged by a batch, or by a continuous reaction process in which the tolylene dicarbamate is charged into the inert solvent containing the catalyst under reduced pressure.

In the thermal decomposition, a tolylene diisocyanate and an alcohol are produced and, for example, allophanate, amines, urea, carbonate, carbamate, and carbon dioxide may also be produced by a side reaction in some cases. Therefore, if necessary, the tolylene isocyanate thus produced is purified by a known method.

The isomer ratio of the thus-obtained tolylene diisocyanate is the above-described target isomer ratio, and the proportion (molar ratio) of the 2,4-tolylene diisocyanate is lower than the proportion (molar ratio) of 2,4-diaminotoluene in the mixed diaminotoluene used as the raw material.

If the yield of the tolylene diisocyanate increases in the reaction, the proportion (molar ratio) of 2,4-tolylene diisocyanate in the tolylene diisocyanate increases as well.

The alcohol (the above formula (5)) obtained by the thermal decomposition is separated and recovered, and thereafter preferably used as a raw material component for the carbamate-forming reaction.

Then, in this method, the tolylene diisocyanate and the alcohol are removed from the decomposition solution resulting from the thermal decomposition reaction of the tolylene dicarbamate, and the solvent is separated therefrom as required, as a result of which isocyanate residues are obtained. The separated solvent can be again used for the thermal decomposition.

That is, for example, in the case where tolylene diisocyanate is produced by producing tolylene dicarbamate by reaction of mixed diaminotoluene, urea and/or N-unsubstituted carbamic acid ester and alcohol, and thermally decomposing the tolylene dicarbamate, for example, the obtained tolylene dicarbamate or tolylene diisocyanate, or intermediates thereof may cause unpreferable polymerization reaction such as multimerization, biuretization, or allophanatization in some cases. In such a case, by-products such as urea derivatives (biuret derivatives) or carbamate derivatives (allophanate derivatives) are obtained as isocyanate residues. The isocyanate residues may contain, for example, unreacted urea or carbamate in some cases.

Although these isocyanate residues are usually disposed of, it is required that wastes should be reduced from the viewpoint of global environment or related factors and a method for effectively using recovered isocyanate residues is also desired.

Therefore, in this method, the obtained isocyanate residues are hydrolyzed by contact with high pressure and high temperature water to give diaminotoluene and alcohol.

At this time, the isocyanate residues are often highly viscous and tarry, and thus from the industrial viewpoint, it is desirable to prepare the isocyanate residues in slurry form in order to impart fluidity to the isocyanate residue and transport the slurry. Therefore, a solvent (e.g., carbonate) may be blended with the isocyanate residues if necessary.

Specifically, in this method, the isocyanate residues (and a solvent if necessary) are fed into a known pressure-resistant and heat-resistant tank while high pressure and high temperature water is fed thereinto, and the isocyanate residues are hydrolyzed by contact with high pressure and high temperature water to give diaminotoluene (decomposed diaminotoluene) and alcohol.

The high pressure and high temperature water is water that has been pressurized to a high pressure, specifically, from 3 to 30 MPa, preferably from 6 to 25 MPa, or more preferably from 6 to 20 MPa and heated to a high temperature, specifically, from 190 to 350° C., or preferably from 200 to 300° C. by a known method.

The decomposing pressure (tank internal pressure) of the isocyanate residues is in the range of 3 to 30 MPa, preferably 6 to 25 MPa, or more preferably 6 to 20 MPa. The decomposing temperature (tank internal temperature) of the isocyanate residues is in the range of 190 to 350° C., or preferably 200 to 300° C.

As the high pressure and high temperature water, a hydrolytic ratio (a mass ratio of high pressure and high temperature water/isocyanate residues) is controlled to, for example, 0.5 to 30, or preferably 1 to 15.

As a result of this, the isocyanate residues are hydrolyzed with the high pressure and high temperature water to produce diaminotoluene (decomposed diaminotoluene) as a decomposition product. In such hydrolysis, carbon dioxide, etc. are also by-produced.

At this time, when the isocyanate residues to be decomposed are those obtained by thermally decomposing the tolylene dicarbamate produced by the reaction of mixed diaminotoluene, urea and/or N-unsubstituted carbamic acid ester, and alcohol as described above, the diaminotoluene (decomposed diaminotoluene) contains 2,4-diaminotoluene and/or 2,6-diaminotoluene preferably at the above-described second isomer ratio.

Specifically, the isomer ratio of the thus-obtained decomposed diaminotoluene is preferably such that the proportion (molar ratio) of 2,4-diaminotoluene is higher than the proportion (molar ratio) of 2,4-diaminotoluene in the mixed diaminotoluene and also higher than the proportion (molar ratio) of 2,4-tolylene diisocyanate in the target isomer ratio of the tolylene diisocyanate.

As the isomer ratio of the decomposed diaminotoluene, specifically, the proportion (molar ratio) of 2,4-diaminotoluene is, for example, 80 or greater, preferably 85 or greater, or more preferably 90 or greater. Also, the proportion (molar ratio) of 2,6-diaminotoluene is for example, 20 or less, preferably 15 or less, or more preferably 10 or less.

Then, the decomposed diaminotoluene is separated and recovered, and thereafter preferably used in the above-described tolylene dicarbamate production as a second diaminotoluene.

Any known method may be used to separate the decomposed diaminotoluene. Preferably, distillation is used.

According to the method for producing tolylene diisocyanate described above, a first diaminotoluene and a second diaminotoluene having different 2,4-diaminotoluene/2,6-diaminotoluene isomer ratios are mixed to prepare mixed diaminotoluene, and the mixed diaminotoluene is carbamated and thermally decomposed, and therefore tolylene diisocyanate containing 2,4-tolylene diisocyanate and 2,6-tolylene diisocyanate at the target isomer ratio can be obtained.

In particular, in this method, the proportion of 2,4-tolylene diisocyanate of the tolylene diisocyanate obtained by carbamating and thermally decomposing the mixed diaminotoluene is lower than the proportion of 2,4-diaminotoluene in the mixed diaminotoluene, whereas the proportion of 2,4-diaminotoluene in the decomposed diaminotoluene obtained by hydrolyzing the isocyanate residues is higher than the proportion of 2,4-diaminotoluene in the mixed diaminotoluene. Accordingly, by using the decomposed diaminotoluene, the isomer ratio of the obtained tolylene diisocyanate can be adjusted to the target isomer ratio.

FIG. 1 is a schematic configuration diagram showing an embodiment of a plant in which the method for producing tolylene diisocyanate of the present invention is used.

An embodiment of a plant in which the method for producing tolylene diisocyanate described above is industrially carried out will now be described with reference to FIG. 1.

In FIG. 1, this plant 1 is a tolylene diisocyanate production system for producing tolylene diisocyanate by a urea method, and includes a mixer system 35, a reaction system 2, a light-boiling distillation system 3, a thermal decomposition system 4, a distillation system 7, a hydrolysis system 5, and a purification system 6.

The mixer system 35 is provided in the plant 1 in order to mix a first diaminotoluene and a second diaminotoluene to produce mixed diaminotoluene.

The mixer system 35 includes a mixing tank 38, a first diaminotoluene feed pipe 36 and a second diaminotoluene feed pipe 37 that are connected to the mixing tank 38.

The mixing tank 38 is a mixing tank for mixing a first diaminotoluene and a second diaminotoluene to produce mixed diaminotoluene, and is composed of a heat-resistant and pressure-resistant vessel whose temperature and pressure can be controlled.

Although not shown, the mixing tank 38 may be provided with, for example, an inert gas feed pipe for substituting the inside of the mixing tank 38 with inert gas (i.e., nitrogen gas), a stirrer for stirring within the mixing tank 38, if necessary.

The first diaminotoluene feed pipe 36 is a first diaminotoluene feed line for feeding a first diaminotoluene to the mixing tank 38, and its downstream end is connected to the mixing tank 38. Although not shown, the upstream end thereof is connected to a first diaminotoluene introducing line for introducing a first diaminotoluene.

The second diaminotoluene feed pipe 37 is a second diaminotoluene feed line for feeding a second diaminotoluene to the mixing tank 38, and its downstream end is connected to the mixing tank 38. Also, the upstream end thereof is connected to the downstream end of a decomposed diaminotoluene reflux pipe 25, which will be described later, for introducing decomposed diaminotoluene used as a second diaminotoluene.

The reaction system 2 is provided in the plant 1 in order to produce tolylene dicarbamate by reaction of mixed diaminotoluene, urea and/or N-unsubstituted carbamic acid ester and alcohol.

The reaction system 2 includes a reaction tank 8, a mixed diaminotoluene feed pipe 9, a urea feed pipe 10, a carbamic acid ester feed pipe 12 and an alcohol feed pipe 11 that are connected to the reaction tank 8.

The reaction tank 8 is a carbamate-forming reaction tank for subjecting mixed diaminotoluene, urea and/or N-unsubstituted carbamic acid ester, and alcohol to carbamate-forming reaction to produce tolylene dicarbamate, and is composed of a heat-resistant and pressure-resistant vessel whose temperature and pressure can be controlled.

Although not shown, the reaction tank 8 may be provided with, for example, a catalyst feed pipe for feeding a catalyst to the reaction tank 8, an inert gas feed pipe for substituting the inside of the reaction tank 8 with inert gas (i.e., nitrogen gas), a stirrer for stirring within the reaction tank 8, an ammonia drain pipe that distills by-produced ammonia out of the system, if necessary.

The mixed diaminotoluene feed pipe 9 is a mixed diaminotoluene feed line for feeding mixed diaminotoluene to the reaction tank 8, and its downstream end is connected to the reaction tank 8. Also, the upstream end thereof is connected to the mixing tank 38 of the mixer system 35.

The urea feed pipe 10 is a urea feed line for feeding urea to the reaction tank 8, and its downstream end is connected to the reaction tank 8. Although not shown, the upstream end thereof is connected to a urea introducing line for introducing urea.

The carbamic acid ester feed pipe 12 is an N-unsubstituted carbamic acid ester feed line for feeding N-unsubstituted carbamic acid ester to the reaction tank 8, and its downstream end is connected to the reaction tank 8. Although not shown, upstream end thereof is connected to an N-unsubstituted carbamic acid ester introducing line for introducing N-unsubstituted carbamic acid ester.

The downstream end of a carbamic acid ester reflux pipe 30, which will be described later, is connected to the carbamic acid ester feed pipe 12 at a position along the flow direction thereof.

The alcohol feed pipe 11 is an alcohol feed line for feeding alcohol to the reaction tank 8, and its downstream end is connected to the reaction tank 8. Although not shown, the upstream end thereof is connected to an alcohol introducing line for introducing alcohol.

The downstream end of a first alcohol reflux pipe 31, the downstream end of a second alcohol reflux pipe 32, and the downstream end of a third alcohol reflux pipe 34, all of which will be described later, are connected to the alcohol feed pipe 11 at positions along the flow direction thereof.

The light-boiling distillation system 3 is provided in the plant 1 in order to separate low boiling components (light-boiling fractions) such as excess (unreacted) alcohol, urea and/or N-unsubstituted carbamic acid ester; as well as alcohol and N-unsubstituted carbamic acid ester which are by-products, from the reaction solution obtained in the reaction tank 8.

The light-boiling distillation system 3 includes a light-boiling distillation tank 13 and a first reaction solution transporting pipe 14 connected to the light-boiling distillation tank 13.

The light-boiling distillation tank 13 is a distillation tank for distilling the low boiling components from the reaction solution obtained in the reaction system 2, and is composed of a heat-resistant and pressure-resistant vessel whose temperature and pressure can be controlled.

The first reaction solution transporting pipe 14 is a first reaction solution transporting line for transporting the reaction solution produced in the reaction system 2 to the light-boiling distillation tank 13, and its downstream end is connected to the light-boiling distillation tank 13. Also, the upstream end thereof is connected to the reaction tank 8 of the reaction system 2.

The thermal decomposition system 4 is provided in the plant 1 in order to thermally discompose the reaction solution into tolylene diisocyanate and alcohol.

The thermal decomposition system 4 includes a thermal decomposition tank 15, a second reaction solution transporting pipe 16 and an isocyanate drain pipe 17 that are connected to the thermal decomposition tank 15.

The thermal decomposition tank 15 is a decomposition tank for thermally decomposing the reaction solution obtained in the reaction system 2 into tolylene diisocyanate and alcohol by heating the reaction solution, and is composed of a heat-resistant and pressure-resistant vessel whose temperature and pressure can be controlled.

Although not shown, the thermal decomposition tank 15 may be provided with, for example, a solvent feed pipe for feeding a solvent to the thermal decomposition tank 15, if necessary.

The second reaction solution transporting pipe 16 is a second reaction solution transporting line for transporting the reaction solution from which light-boiling fractions have been distilled in the light-boiling distillation system 3 to the thermal decomposition tank 15, and its downstream end is connected to the thermal decomposition tank 15. Also, the upstream end thereof is connected to the light-boiling distillation tank 13 of the light-boiling distillation system 3.

The isocyanate drain pipe 17 is an isocyanate drain line for draining the tolylene diisocyanate obtained as a result of thermal decomposition of the reaction solution out of the plant 1, and its upstream end is connected to the thermal decomposition tank 15. Although not shown, the downstream end thereof is connected to an isocyanate purifying line for purifying tolylene diisocyanate.

The distillation system 7 is provided in the plant 1 in order to separate alcohol and N-unsubstituted carbamic acid ester from the low boiling components (light-boiling fractions) obtained in the light-boiling distillation tank 13.

The distillation system 7 includes a distillation column 28 and a light-boiling fraction transporting pipe 27 connected to the distillation column 28.

The distillation column 28 is a separation column for roughly separating N-unsubstituted carbamic acid ester, and further roughly separating alcohol from the low boiling components obtained in the light-boiling distillation system 3, and is composed of a known distillation column.

The light-boiling fraction transporting pipe 27 is a light-boiling fraction transporting line for transporting the light-boiling fractions obtained in the light-boiling distillation system 3 to the distillation system 7, and its downstream end is connected to the distillation column 28. Also, the upstream end thereof is connected to the light-boiling distillation tank 13 of the light-boiling distillation system 3.

The hydrolysis system 5 is provided in the plant 1 in order to hydrolyze the isocyanate residues obtained in the thermal decomposition system 4 with high pressure and high temperature water to give diaminotoluene (decomposed diaminotoluene) and alcohol.

The hydrolysis system 5 includes a hydrolysis tank 18, an isocyanate residue transporting pipe 19 and a water feed pipe 20 that are connected to the hydrolysis tank 18.

The hydrolysis tank 18 is a hydrolysis tank for hydrolyzing the isocyanate residues into diaminotoluene (decomposed diaminotoluene) and alcohol by contact of the isocyanate residues with high pressure and high temperature water, so as to give a hydrolyzed solution, and is composed of a heat-resistant and pressure-resistant vessel whose temperature and pressure can be controlled.

The hydrolysis tank 18 is also provided with a drain pipe 33 for draining, from the plant 1, carbon dioxide by-produced as a result of hydrolysis of the isocyanate residues and water used in the hydrolysis.

Although not shown, the hydrolysis tank 18 may be provided with, for example, a stirrer for stirring within the hydrolysis tank 18, if necessary.

The isocyanate residue transporting pipe 19 is an isocyanate residue transporting line for transporting the isocyanate residues generated in the thermal decomposition system 4 to the hydrolysis tank 18, and its downstream end is connected to the hydrolysis tank 18. Also, the upstream end thereof is connected to the thermal decomposition tank 15 of the thermal decomposition system 4.

Also, if necessary, a solvent feed system for feeding a solvent to the isocyanate residue transporting pipe 19 and a residue pressure-feed pump (not shown) for pressure-transporting the isocyanate residues toward the hydrolysis tank 18 may be provided at positions along the isocyanate residue transporting pipe 19. Furthermore, if necessary, a residue heater (not shown) for heating the isocyanate residues may be provided on the downstream side of the residue pressure-feed pump (not shown).

The water feed pipe 20 is a water feed line for feeding high pressure and high temperature water to the hydrolysis tank 18, and is composed of a heat-resistant and pressure-resistant pipe. The downstream end of the water feed pipe 20 is connected to the hydrolysis tank 18, and the upstream end thereof is connected to a water feed line (not shown) for feeding water such as recovered process water or ion-exchange water.

Also, a water pressure-feed pump 23 for pressure-transporting high pressure and high temperature water toward the hydrolysis tank 18 is provided at a position along the water feed pipe 20. Furthermore, a water heater 22 for heating the water is provided on the downstream side of the water pressure-feed pump 23 along the water feed pipe 20.

The purification system 6 is provided in the plant 1 in order to separate and purify diaminotoluene (decomposed diaminotoluene) and alcohol from the hydrolyzed solution containing the diaminotoluene (decomposed diaminotoluene) and alcohol obtained in the hydrolysis tank 18 and further containing the components (secondary residues) that remain without being decomposed into diaminotoluene (decomposed diaminotoluene), alcohol, etc.

The purification system 6 includes a purification tank 24, and a hydrolyzed solution transporting pipe 21 and a secondary residue drain pipe 26 that are connected to the purification tank 24.

The purification tank 24 is a purification tank for separating and purifying diaminotoluene (decomposed diaminotoluene) and alcohol from the hydrolyzed solution obtained in the hydrolysis system 5, and is composed of a heat-resistant and pressure-resistant vessel whose temperature and pressure can be controlled.

The hydrolyzed solution transporting pipe 21 is a hydrolyzed solution transporting line for transporting the reaction solution produced in the hydrolysis system 5 to the purification tank 24. The downstream end of the hydrolyzed solution transporting pipe 21 is connected to the purification tank 24, and the upstream end thereof is connected to the hydrolysis tank 18 of the hydrolysis system 5.

The secondary residue drain pipe 26 is a secondary residue drain line for draining the components (secondary residues) that remain without being decomposed into diaminotoluene (decomposed diaminotoluene), alcohol, etc. when the isocyanate residues are brought into contact with high pressure and high temperature water, and its upstream end is connected to the purification tank 24. Although not shown, the downstream end thereof is connected to a secondary residue storage tank where secondary residues are stored.

The plant 1 further includes the decomposed diaminotoluene reflux pipe 25, the first alcohol reflux pipe 31, the second alcohol reflux pipe 32, the third alcohol reflux pipe 34 and the carbamic acid ester reflux pipe 30.

The decomposed diaminotoluene reflux pipe 25 is a decomposed diaminotoluene reflux line for refluxing the decomposed diaminotoluene, which has been separated from the hydrolyzed solution and then purified in the purification system 6, to the second diaminotoluene feed pipe 37 of the reaction system 2. The upstream end of the decomposed diaminotoluene reflux pipe 25 is connected to the purification tank 24, and the downstream end thereof is connected to the upstream end of the second diaminotoluene feed pipe 37.

The first alcohol reflux pipe 31 is a first alcohol reflux line for refluxing the alcohol, obtained as a result of thermal decomposition of the tolylene diisocyanate in the thermal decomposition system 4, to the alcohol feed pipe 11 of the reaction system 2. The upstream end of the first alcohol reflux pipe 31 is connected to the thermal decomposition tank 15, and the downstream end thereof is connected at a position along the flow direction of the alcohol feed pipe 11.

The second alcohol reflux pipe 32 is a second alcohol reflux line for refluxing the alcohol, which has been separated from the hydrolyzed solution and purified in the purification system 6, to the alcohol feed pipe 11 of the reaction system 2. The upstream end of the second alcohol reflux pipe 32 is connected to the purification tank 24, and the downstream end thereof is connected at a position along the flow direction of the alcohol feed pipe 11.

The third alcohol reflux pipe 34 is a third alcohol reflux line for refluxing the alcohol, obtained as a result of distillation of the low boiling components (light-boiling fractions) in the distillation system 7, to the alcohol feed pipe 11 of the reaction system 2. The upstream end of the third alcohol reflux pipe 34 is connected to the distillation column 28, and the downstream end thereof is connected at a position along the flow direction of the alcohol feed pipe 11.

The carbamic acid ester reflux pipe 30 is a carbamic acid ester reflux line for refluxing the N-unsubstituted carbamic acid ester, obtained as a result of distillation of the low boiling components (light-boiling fractions) in the distillation system 7, to the carbamic acid ester feed pipe 12 of the reaction system 2. The upstream end of the carbamic acid ester reflux pipe 30 is connected to the distillation column 28, and the downstream end thereof is connected at a position along the flow direction of the carbamic acid ester feed pipe 12.

Next is a description of a method in which, in the plant 1, tolylene dicarbamate and tolylene diisocyanate are produced to obtain isocyanate residues, the resulting isocyanate residues are hydrolyzed, and the resulting diaminotoluene and alcohol are again used as raw material components for the carbamate-forming reaction.

In this method, first, mixed diaminotoluene is produced in the mixer system 35.

For production of the mixed diaminotoluene, the mixer system 35 is continuously operated such that, as will be described late; a first diaminotoluene is pressure-transported from the first diaminotoluene feed pipe 36 and a second diaminotoluene (decomposed diaminotoluene) is pressure-transported from the second diaminotoluene feed pipe 37 via the decomposed diaminotoluene reflux pipe 25 at the above-described ratio, and continuously fed to the mixing tank 38.

As a result, mixed diaminotoluene containing 2,4-diaminotoluene and 2,6-diaminotoluene at the above-described ratio is produced.

Then, in this method, tolylene dicarbamate is produced in the reaction system 2.

For production of the tolylene dicarbamate, the reaction system 2 is continuously operated such that the mixed diaminotoluene, urea and/or N-unsubstituted carbamic acid ester, and alcohol as raw materials for tolylene dicarbamate are pressure-transported from the mixed diaminotoluene feed pipe 9, the urea feed pipe 10 and/or the carbamic acid ester feed pipe 12 and the alcohol feed pipe 11 at the above-described ratio and continuously fed to the reaction tank 8. If necessary, a catalyst may be fed from a catalyst feed pipe (not shown) together with these raw material components.

Then, in this method, in the reaction tank 8, the mixed diaminotoluene, urea and/or N-unsubstituted carbamic acid ester, and alcohol are subjected to carbamate-forming reaction, whereby a reaction solution containing tolylene dicarbamate, and alcohol and N-unsubstituted carbamic acid ester which have been by-produced is obtained.

The thus-obtained reaction solution is fed to the first reaction solution transporting pipe 14, and pressure-transported to the light-boiling distillation system 3.

Next, in this method, in the light-boiling distillation system 3 (the light-boiling distillation tank 13), low boiling components (light-boiling fractions) including, for example, excess (unreacted) alcohol, urea and/or N-unsubstituted carbamic acid ester, and alcohol and N-unsubstituted carbamic acid ester which have been by-produced, etc. are separated from the reaction solution.

The light-boiling fractions separated in the light-boiling distillation tank 13 are introduced into the light-boiling fraction transporting pipe 27 and fed to the distillation system 7.

Then, in this method, the low boiling components (light-boiling fractions) fed to the distillation system 7 are distilled in the distillation column 28, whereby the N-unsubstituted carbamic acid ester and alcohol (including excess (unreacted) alcohol and by-produced alcohol) are roughly separated.

The roughly separated N-unsubstituted carbamic acid ester is introduced into the carbamic acid ester reflux pipe 30 and refluxed to the carbamic acid ester feed pipe 12, whereby the N-unsubstituted carbamic acid ester is fed to the reaction tank 8.

Also, the roughly separated alcohol is introduced into the third alcohol reflux pipe 34 and refluxed to the alcohol feed pipe 11, whereby the alcohol is fed to the reaction tank 8.

Meanwhile, the residual reaction solution from which light-boiling fractions have been separated in the light-boiling distillation system 3 is fed to the second reaction solution transporting pipe 16 and pressure-transported to the thermal decomposition system 4.

Next, in this method, in the thermal decomposition system 4, the reaction solution is thermally decomposed.

For thermal decomposition of the reaction solution, the thermal decomposition system 4 is continuously operated such that the reaction solution fed via the second reaction solution transporting pipe 16 is heated and thermally decomposed under the above-described conditions in the thermal decomposition tank 15.

Tolylene diisocyanate and alcohol are thereby obtained as decomposition solutions, and isocyanate residues are also obtained together with the tolylene diisocyanate and the alcohol.

The tolylene diisocyanate obtained in the thermal decomposition tank 15 is drained via the isocyanate drain pipe 17 and transported to the isocyanate purifying line (not shown).

On the other hand, the alcohol obtained in the thermal decomposition tank 15 is, after separated from the decomposition solution, introduced into the first alcohol reflux pipe 31 and refluxed to the alcohol feed pipe 11. The alcohol is thereby fed to the reaction tank 8.

The isocyanate residues obtained in the thermal decomposition tank 15 are fed to the isocyanate residue transporting pipe 19 and pressure-transported to the hydrolysis system 5.

At this time, in the isocyanate residue transporting pipe 19, if necessary, a solvent (carbonate etc.) may be fed from the solvent feed system (not shown) and blended with the isocyanate residues to make the highly viscous tarry isocyanate residues into a slurry to ensure fluidity. The thus-obtained isocyanate residues in the form of a slurry is pressure-transported to the hydrolysis system 5.

Next, in this method, in the hydrolysis system 5, the isocyanate residues are hydrolyzed.

For hydrolysis of the isocyanate residues, the hydrolysis system 5 is continuously operated such that the isocyanate residues fed from the thermal decomposition system 4 (the thermal decomposition tank 15) via the isocyanate residue transporting pipe 19 are decomposed under the above-described conditions in the hydrolysis tank 18.

Specifically, in this method, the isocyanate residues, while being pressurized to a feed pressure of, for example, 3 to 30 MPa and heated to a feed temperature of, for example, 190 to 350° C., are fed to the hydrolysis tank 18 via the isocyanate residue transporting pipe 19.

Meanwhile, the water flowing from the water feed line into the water feed pipe 20 is pressure-transported toward the hydrolysis tank 18 through the water feed pipe 20 by the water pressure-feed pump 23 and heated by the water heater 22. The water thereby turns into high pressure and high temperature water that has been pressurized to 3 to 30 MPa and heated to 190 to 350° C., and then flows into the hydrolysis tank 18.

The hydrolysis tank 18 is controlled to have, for example, a tank internal temperature (decomposing temperature) of 190 to 350° C., and a tank internal pressure (decomposing pressure) of 3 to 30 MPa. Also, the mass ratio of high pressure and high temperature water to isocyanate residues is controlled to, for example, 0.5 to 30 under control of the residue pressure-feed pump (not shown) and the water pressure-feed pump 23.

Accordingly, in the hydrolysis tank 18, the isocyanate residues are continuously hydrolyzed with the high pressure and high temperature water into diaminotoluene (decomposed diaminotoluene) and alcohol as decomposition products, and a hydrolyzed solution containing the diaminotoluene and the alcohol and components (secondary residues) that remain without being decomposed into the diaminotoluene, the alcohol, etc.

The by-produced carbon dioxide and the water used in the hydrolysis are drained out of the plant 1 via the drain pipe 33.

The hydrolyzed solution containing the diaminotoluene and the alcohol and the secondary residues is fed to the hydrolyzed solution transporting pipe 21 and pressure-transported to the purification system 6.

Next, in this method, in the purification system 6 (the purification tank 24), the diaminotoluene and the alcohol are separated from the hydrolyzed solution.

The separated diaminotoluene (decomposed diaminotoluene) is introduced into the decomposed diaminotoluene reflux pipe 25 and refluxed to the second diaminotoluene feed pipe 37. The decomposed diaminotoluene is thereby fed to the mixing tank 38 as a second diaminotoluene.

Also, the separated alcohol is introduced into the second alcohol reflux pipe 32 and refluxed to the alcohol feed pipe 11. The alcohol is thereby fed to the reaction tank 8.

The secondary residues obtained in the purification tank 24 are transported to the secondary residue storage tank (not shown) via the secondary residue drain pipe 26 so as to be temporarily stored in the secondary residue storage tank (not shown), and are thereafter, for example, disposed of by incineration.

With the plant 1 described above, a first diaminotoluene and a second diaminotoluene having different 2,4-diaminotoluene/2,6-diaminotoluene isomer ratios are mixed to prepare mixed diaminotoluene, and the mixed diaminotoluene is carbamated and thermally decomposed, and therefore tolylene diisocyanate containing 2,4-tolylene diisocyanate and 2,6-tolylene diisocyanate at a target isomer ratio can be obtained.

Also, with the plant 1, isocyanate can be continuously produced, and at the same time, isocyanate residues can be decomposed at a time and the resulting decomposed diaminotoluene and alcohol can be refluxed and efficiently used.

Furthermore, with the plant 1, alcohol and N-unsubstituted carbamic acid ester obtained as by-products of carbamate-forming reaction can be separated, and the alcohol and N-unsubstituted carbamic acid ester can be refluxed and efficiently used.

Up to here, the method for producing tolylene diisocyanate has been described. In the plant 1 described above, if necessary, a pre-treatment system for carrying out pre-treatment steps such as a dehydration step, a post-treatment system for carrying out post-treatment steps such as an intermediate step, a distillation step, a filtration step, a purification step and a recovering step may be provided at appropriate positions.

Also, in the foregoing, the upstream end of the second diaminotoluene feed pipe 37 and the downstream end of the decomposed diaminotoluene reflux pipe 25 are directly connected, and only decomposed diaminotoluene is used as a second diaminotoluene. However, instead of connecting the downstream end of the decomposed diaminotoluene reflux pipe 25 to the second diaminotoluene feed pipe 37, it is possible to, for example, as shown by a broken line in FIG. 1, connect the upstream end of the second diaminotoluene feed pipe 37 to a second diaminotoluene introducing line (not shown) for introducing a second diaminotoluene, and separately feed a second diaminotoluene from the second diaminotoluene feed pipe 37 to the mixer system 35.

EXAMPLES

Next, the present invention will be described in further detail by way of examples, but the present invention is not limited thereto.

Preparation Example 1

Carbamate Producing Step

A 1-liter SUS autoclave equipped with a pressure control valve, a reflux condenser, a gas-liquid separator, and a stirrer was charged with a first diaminotoluene (2,4-diaminotoluene/2,6-diaminotoluene=80/20 (molar ratio)) (122 g: 1 mol), butyl carbamate (333 g: 2.85 mol) and 1-butanol (211 g: 2.85 mol), and zinc p-toluenesulfonate (1.0 g: 2.5 mmol) as a catalyst. These were stirred at 500 rpm with a nitrogen gas allowed to flow at 1 liter per minute, while the internal pressure was controlled to maintain the reaction temperature at 200° C. by the pressure control valve, and were allowed to react for eight hours to give a reaction solution.

A portion of the reaction solution was sampled and quantified, and as a result it was confirmed that tolylene dicarbamate was obtained at a yield of 95 mol % as the total amount of 2,4-bis(butoxycarbonylamino)toluene (2,4-tolylene dicarbamate) and 2,6-bis(butoxycarbonylamino)toluene (2,6-tolylene dicarbamate).

(Vacuum Distillation of Light-Boiling Fractions)

A 500-ml glass four-neck flask equipped with a stirrer and a condenser tube was charged with 387.77 g of the reaction solution obtained by the above-described carbamnate-forming reaction, and while the charged solution was stirred at 200 rpm, the pressure in the vessel was reduced to 2 kPa with a vacuum pump. The temperature in the vessel was increased to 100° C. with circulation water of 25° C. flowing through the condenser tube, so as to condense the carbamate-forming reaction solution, and 125.44 g of light-boiling fractions were distilled.

The distilled light-boiling fractions were analyzed by a high-performance liquid chromatograph (HPLC) and a gas chromatograph (GC), and as a result it was confirmed that butanol was the main component. Subsequently, the temperature of the circulation water was set to 70° C., and the temperature in the vessel was increased to 180° C. so as to condense the carbamate-forming reaction solution, and 195.89 g of brown concentrate and 63.19 g of light-boiling fractions were obtained.

(Thermal Decomposition of Carbamate, and Separation and Recovery of Isocyanate Residues)

A 500-ml glass four-neck flask equipped with a stirrer and a rectifying column having a reflux pipe at its upper portion was charged with 196 g of the concentrate obtained in Vacuum Distillation of Light-Boiling Fractions above and 196 g of barrel process oil B-05 (manufactured by Matsumura Oil Co., Ltd.) as a solvent. While the charged mixture was stirred at 230 rpm with the temperature of the circulation water in the reflux pipe being set to 90° C., the pressure in the system was reduced to 133 hPa with a vacuum pump.

Next, the temperature was increased by setting the temperature of the thermometer in the reactor to 230° C., so as to increase the temperature at the top of the column. At this time, it was confirmed that tolylene diisocyanate began to condense in the reflux pipe. Then, the reflux ratio was set to 5 (=reflux for 10 seconds/distillation for 2 seconds) to distill off the reflux liquid.

It was confirmed, 240 minutes after the temperature increase, that the distillation had completed. Then, the heating was stopped and the reaction solution was filtered with 5A filter paper and separated into a filtrate and a filter residue.

The yield of the tolylene diisocyanate obtained as the reflux liquid was quantified by HPLC and found to be 78 mol % with respect to the first diaminotoluene. The isomer ratio was 2,4-tolylene diisocyanate/2,6-tolylene diisocyanate=76/24 (molar ratio).

(Production of Decomposed Diaminotoluene)

A 36-mL SUS autoclave equipped with a thermocouple and a pressure regulating valve was charged with 6 g of the filter residue, and the system was filled with ion exchange water. The reactor was placed in an electric furnace, and the charged mixture was allowed to react for 20 minutes while the internal pressure was adjusted with the pressure regulating valve so that the reaction temperature and the internal pressure were maintained at 260° C. and 20 MPa, respectively. At this time, the hydrolytic ratio (ion exchange water/filter residue) was set to 5.

After the reactor was cooled to room temperature, a portion of the reaction solution was sampled and quantified by HPLC. As a result, the recovery rate of the diaminotoluene (decomposed diaminotoluene) was 99 mol %. Also, the isomer ratio of the decomposed diaminotoluene was 2,4-diaminotoluene/2,6-diaminotoluene=95/5 (molar ratio).

Example 1

Mixed diaminotoluene was obtained by mixing 100 g of first diaminotoluene (2,4-diaminotoluene/2,6-diaminotoluene=80/20 (molar ratio)) and 21 g of decomposed diaminotoluene (2,4-diaminotoluene/2,6-diaminotoluene=95/5 (molar ratio)) produced in Preparation Example 1 as a second diaminotoluene (mixing step).

The isomer ratio of the obtained mixed diaminotoluene was 2,4-diaminotoluene/2,6-diaminotoluene=82.6/17.4 (molar ratio).

Tolylene dicarbamate was produced in the same manner as in Preparation Example 1, except that the mixed diaminotoluene was used in place of the first diaminotoluene. It was confirmed that tolylene dicarbamate was obtained at a yield of 95 mol % as the total amount of 2,4-bis(butoxycarbonylamino)toluene (2,4-tolylene dicarbamate) and 2,6-bis(butoxycarbonylamino)toluene (2,6-tolylene dicarbamate).

Also, vacuum distillation of light-boiling fractions was performed in the same manner as in Preparation Example 1, except that the obtained tolylene dicarbamate was used, and then the obtained concentrate was thermally decomposed to give tolylene diisocyanate and a filter residue.

The yield of the obtained tolylene diisocyanate was quantified by HPLC and found to be 94.4 mol % with respect to the first diaminotoluene in the mixed diaminotoluene. The isomer ratio was 2,4-tolylene diisocyanate/2,6-tolylene diisocyanate=79/21 (molar ratio).

The filter residue obtained above was hydrolyzed in the same manner as in Preparation Example 1, and a reaction solution was obtained.

A portion of the reaction solution was sampled and quantified by HPLC. As a result, the recovery rate of the diaminotoluene (decomposed diaminotoluene) was 99 mol %. Also, the isomer ratio of the decomposed diaminotoluene was 2,4-diaminotoluene/2,6-diaminotoluene=95/5 (molar ratio).

Example 2

Tolylene dicarbamate was produced in the same manner as in Example 1, except that 27 g of the decomposed diaminotoluene (second diaminotoluene) obtained in Preparation Example 1 was blended with 100 g of the first diaminotoluene. It was confirmed that tolylene dicarbamate was obtained at a yield of 95 mol % as the total amount of 2,4-bis(butoxycarbonylamino)toluene (2,4-tolylene dicarbamate) and 2,6-bis(butoxycarbonylamino)toluene (2,6-tolylene dicarbamate).

The isomer ratio of the mixed diaminotoluene was 2,4-diaminotoluene/2,6-diaminotoluene=83.2/16.8 (molar ratio).

Also, vacuum distillation of light-boiling fractions was performed in the same manner as in Example 1, except that the obtained tolylene dicarbamate was used, and then the obtained concentrate was thermally decomposed to give tolylene diisocyanate and a filter residue.

The yield of the obtained tolylene diisocyanate was quantified by HPLC and found to be 99.1 mol % with respect to the first diaminotoluene in the mixed diaminotoluene. The isomer ratio was 2,4-tolylene diisocyanate/2,6-tolylene diisocyanate=80/20 (molar ratio).

The filter residue obtained above was hydrolyzed in the same manner as in Example 1, and a reaction solution was obtained.

A portion of the reaction solution was sampled and quantified by HPLC. As a result, the recovery rate of the diaminotoluene (decomposed diaminotoluene) was 99 mol %. Also, the isomer ratio of the decomposed diaminotoluene was 2,4-diaminotoluene/2,6-diaminotoluene=95/5 (molar ratio).

Preparation Example 2

Tolylene dicarbamate was obtained in the same manner as in Preparation Example 1, except that the reaction time in the carbamate-forming reaction was set to 10 hours. It was confirmed that tolylene dicarbamate was obtained at a yield of 98 mol % as the total amount of 2,4-bis(butoxycarbonylamino)toluene (2,4-tolylene dicarbamate) and 2,6-bis(butoxycarbonylamino)toluene (2,6-tolylene dicarbamnate).

Also, vacuum distillation of light-boiling fi-actions was performed in the same manner as in Preparation Example 1, except that the obtained tolylene dicarbamate was used, and then the resulting concentrate was thermally decomposed to give tolylene diisocyanate and a filter residue.

The yield of the obtained tolylene diisocyanate was quantified by HPLC and found to be 88.0 mol %. The isomer ratio was 2,4-tolylene diisocyanate/2,6-tolylene diisocyanate=78/22 (molar ratio).

The filter residue obtained above was hydrolyzed in the same manner as in Preparation Example 1, and a reaction solution was obtained.

A portion of the reaction solution was sampled and quantified by HPLC. As a result, the recovery rate of the diaminotoluene (decomposed diaminotoluene) was 99 mol %. Also, the isomer ratio of the decomposed diaminotoluene was 2,4-diaminotoluene/2,6-diaminotoluene=95/5 (molar ratio).

Example 3

Tolylene dicarbamate was obtained in the same manner as in Example 1, except that the reaction time in the carbamate-forming reaction was set to 10 hours and that 8 g of the decomposed diaminotoluene (second diaminotoluene) obtained in Preparation Example 2 was blended with 100 g of the first diaminotoluene in the mixing step. It was confirmed that tolylene dicarbamate was obtained at a yield of 98 mol % as the total amount of 2,4-bis(butoxycarbonylamino)toluene (2,4-tolylene dicarbamate) and 2,6-bis(butoxycarbonylamino)toluene (2,6-tolylene dicarbamate). The isomer ratio of the mixed diaminotoluene was 2,4-diaminotoluene/2,6-diaminotoluene=81.1/18.9 (molar ratio).

Also, vacuum distillation of light-boiling fractions was performed in the same manner as in Example 1, except that the obtained tolylene dicarbamate was used, and then the obtained concentrate was thermally decomposed to give tolylene diisocyanate and a filter residue.

The yield of the obtained tolylene diisocyanate was quantified by HPLC and found to be 95.0 mol % with respect to the first diaminotoluene in the mixed diaminotoluene. The isomer ratio was 2,4-tolylene diisocyanate/2,6-tolylene diisocyanate=79/21 (molar ratio).

The filter residue obtained above was hydrolyzed in the same manner as in Example 1, and a reaction solution was obtained.

A portion of the reaction solution was sampled and quantified by HPLC. As a result, the recovery rate of the diaminotoluene (decomposed diaminotoluene) was 99 mol %. Also, the isomer ratio of the decomposed diaminotoluene was 2,4-diaminotoluene/2,6-diaminotoluene=95/5 (molar ratio).

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The method for producing tolylene diisocyanate of the present invention can be used as a method for industrially producing tolylene diisocyanate that can be used as a raw material for polyurethane, polyurea or the like.

The invention claimed is:

1. A method for producing tolylene diisocyanate containing 2,4-tolylene diisocyanate and 2,6-tolylene diisocyanate at a target isomer ratio, the method comprising:
    mixing a first diaminotoluene containing 2,4-diaminotoluene and 2,6-diaminotoluene at a first isomer ratio and a second diaminotoluene containing 2,4-diaminotoluene and/or 2,6-diaminotoluene at a second isomer ratio that is different from the first isomer ratio so as to prepare mixed diaminotoluene;
    producing tolylene dicarbamate by reaction of the mixed diaminotoluene, urea and/or N-unsubstituted carbamic acid ester and alcohol; and
    thermally decomposing the tolylene dicarbamate.

2. The method for producing tolylene diisocyanate according to claim 1,
    wherein the first isomer ratio is 2,4-diaminotoluene/2,6-diaminotoluene (molar ratio)=79 to 81/21 to 19,
    the second isomer ratio is set such that a proportion of 2,4-diaminotoluene is higher than a proportion of 2,4-diaminotoluene in the first isomer ratio, and
    in the mixing step, the second diaminotoluene is mixed in an amount of 1 to 30 parts by mass per 100 parts by mass of the first diaminotoluene.

3. The method for producing tolylene diisocyanate according to claim 1,
    wherein the second diaminotoluene is produced by decomposing isocyanate residues, which are obtained by separating tolylene diisocyanate and alcohol from a decomposition solution resulting from the thermal decomposition reaction of the tolylene dicarbamate in the thermal decomposition step, by contact with high pressure and high temperature water.

* * * * *